US005824809A

United States Patent [19]
Smith, III et al.

[11] Patent Number: 5,824,809
[45] Date of Patent: Oct. 20, 1998

[54] ALPHA-AMINOPHOSPHONATES AND PROCESSES FOR THEIR PREPARATION

[75] Inventors: Amos B. Smith, III, Merion, Pa.; Kraig M. Yager; Carol M. Taylor, both of Princeton, N.J.

[73] Assignee: The Trustees of the University of Pennsylvania, Philadelphia, Pa.

[21] Appl. No.: 633,952

[22] Filed: Apr. 15, 1996

Related U.S. Application Data

[62] Division of Ser. No. 214,368, Mar. 17, 1994, Pat. No. 5,508,463.

[51] Int. Cl.$^6$ .................................. C07F 9/06; C07F 9/28
[52] U.S. Cl. ......................... 549/218; 558/145; 558/166; 562/16
[58] Field of Search ................................... 558/145, 166; 562/16; 549/218

[56] References Cited

U.S. PATENT DOCUMENTS

| | | | |
|---|---|---|---|
| 3,268,450 | 8/1966 | Sims et al. | 558/169 |
| 3,314,957 | 4/1967 | Friedman | 558/169 |
| 3,385,914 | 5/1968 | Hindersinn et al. | 558/169 |
| 4,413,125 | 11/1983 | Gaertner | 546/22 |

FOREIGN PATENT DOCUMENTS 0 412 015 S1   2/1991   European Pat. Off. .

OTHER PUBLICATIONS

Dale, et al., "α–Methoxy–α–trifluoromethylphenylacetic Acid, a Versatile Reagent for the Determination of Enantiomeric Composition of Alcohols and Amines", *J. Org. Chem.*, 34, 1969, 2543–2549.

Dhawan, et al., "Optically Active 1–Aminoalkylphosphonic Acids", *Phosphorous and Sulfur*, 1987, 32, 119–144.

Hanessian, et al., "A Versatile Asymmetric Synthesis of α–Amino α–Alkyl–Phosphonic Acidds of High Enantiomeric Purity", *Tetrahedron Letters*, 1990, 31, 6465–6468.

Huber, et al., "Asymmetric Synthesis of α–Aminophosponic Acids", *Helvetica Chimica Acta*, 1985, 68, 1730–1747.

Huber, et al., "Asymmetric Synthesis of N–Hydroxy–α–aminophosphonic and α–Aminophosphonic Acids", *Helvetica Chimica Acta*, 1987, 70, 1461–1476.

Ferrari, et al., "Asymmetric Synthesis of Diethyl α–Amino–α–Alkyl–Phosphonates by Akylation of the Chiral Schiff Base Derived from (+) –Ketopinic Acid and Diethylaminomethyl Phosphite", *Tetrahedron Asymmetry*, 1992, 3, 377–378.

Yokomatsu, et al., "Enantioselective Synthesis of α–Amino Phosponic Acids by an Application of Stereoselective Opening of Homochiral Dioxane Acetals with Triethyl Phosphite", *Tetrahedron Asymmetry*, 1992, 3, 377–378.

Jacquier, et la., "Synthesis of Enantiomerically Pure Aminophosphonic Acids", *Phosphorus and Sulfur*, 1988, 36, 73–77.

Gould, "Synthesis of an Optically Active α–Aminophosponic Acid", *J. Am. Chem. Soc.*,1972, 94, 4361.

Li, S. et al., "Studies on Organophosphorous Compounds. 72. Molecular Mechanics Study of the Structure Effect of Phosphorus–Based Diasteroisomers on the 31P NMR Chemical Shift", *Huaxue Xuebao* 1993, 51(12), 1195–202 in *Chemical Abstracts*, vol. 121, No. 35691.

Yuan, C. et al., "Studies On Organophosphorus Compounds. 78. New Aspects on the Induced Asymmetric Addition of Dialkyl Phosphite to Aldimines–An Effective Synthesis of Chiral 1–Arylphosphonoglycine Derivatives", *Phosphorus, Sulfur Silicon Relat. Elem.* 1993, 81(1–4), 27–35 in *Chemical Abstracts*, vol. 121, No. 57895.

*Primary Examiner*—Michael G. Ambrose
*Attorney, Agent, or Firm*—Woodcock Washburn Kurtz Mackiewicz & Norris LLP

[57] ABSTRACT

Novel α-aminophosphonates are provided along with processes and intermediates for their preparation. In preferred embodiments, scalemic α-aminophosphonates are prepared by the stereoselective addition of phosphite salts to chiral imines.

10 Claims, 1 Drawing Sheet a Crude yield. b Determined by 500-MHz 1H NMR. c Purified Yield. d Trace of 9a detectable. e R = CH₂OH. f Reaction time of 48 h. # In progress.

ALPHA-AMINOPHOSPHONATES AND PROCESSES FOR THEIR PREPARATION

This is a division of application Ser. No. 08/214,368, filed Mar. 17, 1994, now U.S. Pat. No. 5,508,463. +gi

GOVERNMENT SUPPORT

Certain aspects of the invention have been supported by National Institutes of Health Grant 1F32CA60382-01 BIOM.

FIELD OF THE INVENTION

This invention relates to α-aminophosphonic acids and esters (together, α-aminophosphonates), to processes whereby such compounds are prepared by diastereoselective addition of phosphites to chiral imines, and to synthetic intermediates formed during such processes.

BACKGROUND OF THE INVENTION

α-Aminophosphonic acids represent an important class of organic compounds due to their analogy to α-aminocarboxylic acids. Indeed, several synthetic derivatives of α-aminophosphonic acids have pronounced biological activities, including inhibition of proteolytic enzymes and bacterial growth. α-Aminophosphonic acids also have been found in nature as components of hypertensive active tripeptides. Their biological properties are believed to be strongly influenced by the absolute configuration at the α-carbon. For example, the L,L-diastereomer of the antibiotic alafosfalin—an α-aminophosphonate —is considerably more effective than the other three stereoisomers.

Several methods have been devised for preparation of racemic α-aminophosphonates. However, known asymmetric syntheses are predominantly limited by low to moderate enantiomeric excesses, multiple synthetic operations and little choice of absolute stereochemistry. (See, e.g., Dhawan, et al., *Phosphorous and Sulfur* 1987, 32, 119) Thus, there is a need for more general synthetic methods that afford aminophosphonates of high optical purity with choice of side chain and absolute stereochemistry.

OBJECTS OF THE INVENTION

It is one object of the present invention to provide novel α-aminophosphonates.

It is another object of the invention to provide α-aminophosphonates of relatively high optical purity.

It is a further object to provide processes and intermediates for the preparation of novel and chirally pure α-aminophosphonates.

SUMMARY OF THE INVENTION

These and other objects are satisfied by the present invention, which provides novel and/or chirally pure α-aminophosphonates, as well as processes and intermediates for their preparation. In certain embodiments, α-aminophosphonates according to the invention have formula I:

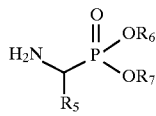

Wherein:

$R_5$ is alkyl having 1 to about 10 carbon atoms; aryl having 6 to about 14 carbon atoms; aralkyl having 7 to about 15 carbon atoms; a naturally occurring amino acid sidechain; or —$(CH_2)_n$—$(CH=CH)_x$—X wherein n is 1–5, x is 0 or 1, and X is hydrogen, alkyl having from 1 to about 10 carbon atoms, or aryl having 6 to about 14 carbon atoms; and $R_6$ and $R_7$ are, independently, H, alkyl having 1 to about 5 carbon atoms, aryl having 6 to about 14 carbon atoms, or aralkyl having 7 to about 15 carbon atoms.

In preferred embodiments, such α-aminophosphonates are in the form of their R-isomers substantially free of their S-isomers or in the form of their S-isomers substantially free of their R-isomers, more preferably in chirally pure form.

In certain embodiments, α-aminophosphonates are prepared by processes whereby primary amine compounds having formula II are contacted with aldehydes having formula $R_5C(O)H$ for a time and under conditions effective to form imines having formula III:

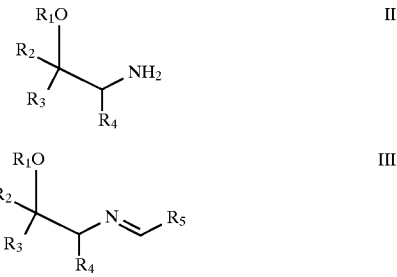

wherein:

$R_1$ is alkyl having 1 to about 10 carbon atoms or alkaryl having 7 to about 15 carbon atoms;

$R_2$ and $R_3$ are, independently, H, alkyl having 1 to about 10 carbon atoms, aryl having 6 to about 14 carbon atoms, or $R_2$ and $R_3$, together, are aryl or cycloalkyl; and $R_4$ is aryl having 6 to about 14 carbon atoms.

The imine compounds are then reacted with phosphites having formula IV (M=metal ion) to form secondary aminophosphonates having formula V ($R_8$=H, alkanoyl having 1 to about 5 carbon atoms, or alkoxycarbonyl having 1 to about 5 carbon atoms). Preferably, compounds having formula V are formed as their R,R-diastereomers. Reduction of the secondary aminophosphonates then is effected to produce corresponding α-aminophosphonates having formula I, preferably in good yield with high enantiomeric excess.

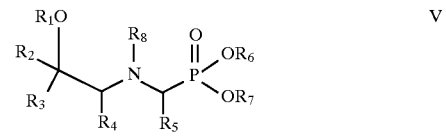

BRIEF DESCRIPTION OF THE DRAWINGS

The numerous objects and advantages of the present invention will be better understood by those skilled in the art by reference to the accompanying FIG. 1, which shows exemplary synthetic routes according to the invention and a tabular summary thereof.

DETAILED DESCRIPTION OF THE PREFERRED EMBODIMENTS

Figure 1:

It has been found in accordance with the invention that scalemic (i.e., enantiomerically enriched)

α-aminophosphonates can be prepared through diastereoselective additions of phosphite anions to chiral imines. Representative synthetic procedures according to the invention are set forth in FIG. 1. In preferred embodiments, the imine R-isomer (e.g., 6a) is used. Addition of phosphite to such compounds produces secondary aminophosphonate R,R- and R,S-diastereomers (e.g., 8a and 9a, respectively) in high yield and high diastereomeric excess in favor of the R,R- or the R,S-diastereomer. Reduction of the secondary aminophosphonates diastereomers, in turn, provides substantially chirally pure α-aminophosphonate R-enantiomers, e.g., 12.

As will be recognized, isomeric (e.g, diastereomeric or enantiomeric) purity is manifested by the presence of one isomer and the absence of its corresponding isomer or isomers, that is, by an excess of one isomer relative to the other(s). In preferred embodiments, compounds of the invention that can exist as isomers are prepared and isolated in the form of a given isomer substantially free of other isomers. It will be recognized that an isomer is substantially free of other isomers when no more than about 20% of such other isomers are present. Preferably no more than about 10 of other isomers are present, more preferably no more than about 5%, even more preferably no more than about 2%. In particularly preferred embodiments, no other isomers are present.

While not wishing to be bound by any particular theory, it is believed that the reaction of chiral imines of formula III with phosphite salts having formula IV proceeds via a cyclic transition state having, for example, structure VI.

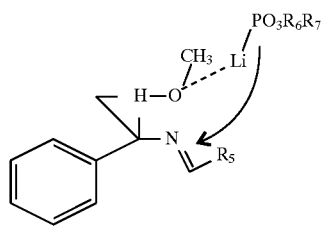

VI

In this model, chelation of the metal cation by the ether oxygen and imine nitrogen creates a rigid five-membered ring in which the phenyl and phosphite groups adopt a trans relationship. The phosphite anion is suitably disposed for addition to the re-face of the imine double bond, leading to a highly stereospecific addition and, hence, to scalemic products.

Chiral imines having formula III preferably are formed by reacting primary amine compounds having formula II with aldehydes having formula $R_5C(O)H$. Such reactions generally are performed by combining the two components as solutions in a nonpolar hydrocarbon solvent such as benzene or toluene at about 0° C. and then allowing the mixture to stir at ambient temperature for about 45 minutes to six hours in the presence of a desiccant such as anhydrous sodium sulfate or magnesium sulfate.

$R_1$ preferably is a group that facilitates internal, bidentate coordination of the ether oxygen and the metal cation in cyclic intermediate VI. Preferably, $R_1$ is alkyl having 1 to about 10 carbon atoms or alkaryl having 7 to about 15 carbon atoms. Alkyl groups according to the invention include straight chain, branched, and cyclic hydrocarbons such as methyl, isopropyl, and cyclohexyl groups. Preferred alkyl groups have 1 to about 5 carbon atoms. Alkaryl groups according to the invention include both alkyl and aryl portions, although the point of attachment of such groups is through an alkyl portion thereof. Benzyl groups provide one example of an alkaryl group. The term aryl is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms. The terms alkyl, alkaryl, and aryl are intended to denote both substituted (e.g., halogenated and hydroxylated) and unsubstituted moieties.

$R_2$, $R_3$, $R_4$, and $R_5$ can be selected from a wide variety of groups, so long as they do not interfere with the above-noted cyclic transition state. $R_2$ and $R_3$ preferably are H, alkyl having 1 to about 10 carbon atoms, aryl having 6 to about 14 carbon atoms. Also, $R_2$ and $R_3$, together, can form an aryl or cycloalkyl group. It is preferred that both $R_2$ and $R_3$ are H or that neither is H. $R_4$ preferably is aryl having 6 to about 14 carbon atoms.

As will be recognized, $R_5$ groups present in α-aminophosphonate compounds of the invention are introduced by selection and use of a corresponding aldehyde starting material. Thus, a wide variety of compounds according to the invention can readily be prepared from well-known and/or commercially available aldehydes. $R_5$ preferably is alkyl having 1 to about 10 carbon atoms; aryl having 6 to about 14 carbon atoms; aralkyl having 7 to about 15 carbon atoms; a naturally occurring amino acid sidechain; or $—(CH_2)_n—(CH=CH)_x—X$ where n is 1–5, x is 0 or 1, and X is hydrogen, alkyl having from 1 to about 10 carbon atoms, or aryl having 6 to about 14 carbon atoms. Representative amino acid sidechains are set forth in Table 1.

TABLE 1

| | |
|---|---|
| $CH_3—$ | $CH_3—CH_2—S—CH_2—CH_2—$ |
| $HO—CH_2—$ | $HO—CH_2—CH_2—$ |
| $C_6H_5—CH_2—$ | $CH_3—CH_2(OH)—$ |
| $HO—C_6H_5—CH_2—$ | $HO_2C—CH_2—NH_2C(O)—CH_2—$ |
| 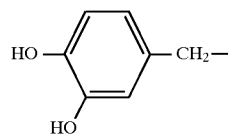 | 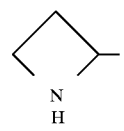 |

TABLE 1-continued

| | |
|---|---|
| [indole-3-CH₂—] structure (3-methylene-1H-indole) | $HCO_2-CH_2-CH_2-$ |
| | $NH_2C(O)-CH_2-CH_2-$ |
| | $(CH_3)_2-CH-$ |
| | $(CH_3)_2-CH-CH_2-$ |
| | $CH_3-CH_2-CH_2-$ |
| [imidazol-4-yl-CH₂—] structure (1H-imidazol-4-ylmethyl) | $H_2N-CH_2-CH_2-CH_2-$ |
| | $H_2N-C(NH)-NH-CH_2-CH_2-CH_2-$ |
| | $H_2N-C(O)-NH-CH_2-CH_2-CH_2-$ |
| | $CH_3-CH_2-CH(CH_3)-$ |
| $HS-CH_2-$ | $CH_3-CH_2-CH_2-CH_2-$ |
| $HO_2C-CH(NH_2)-CH_2-S-S-CH_2-$ | $H_2N-CH_2-CH_2-CH_2-CH_2-$ |
| $CH_3-CH_2-$ | |
| $CH_3-S-CH_2-CH_2-$ | |

Preferably, $R_5$ in formula III does not contain a tertiary carbon atom in the position alpha to the imino carbon atom. It also is preferred that n and x are not both 1 and that n is not 1 when x is 0 and X is aryl. $R_5$ groups of interest include cyclohexyl, cyclohexylmethyl, isopropyl, isovaleryl, n-hexyl, 2-thiomethylethyl, benzyloxymethyl, t-butylpropionate, phenyl, naphthyl, and furyl groups. It is believed that compounds having formula III should not contain a lone tetravalent carbon atom between the imine carbon and an aryl or alkenyl (e.g., CH=CH—X) group. Moreover, where $R_5$ includes more than one tetravalent carbon, it is believed that the tetravalent carbon beta to the imine carbon should not bear electron-withdrawing substituents.

As noted above, secondary aminophosphonates preferably are prepared by diastereoselective additions of phosphite salts having formula IV to chiral imines having formula III. Such reactions generally are performed in polar, aprotic solvents at ambient temperatures under strictly anhydrous conditions in an inert atmosphere such as argon or nitrogen gas. $R_6$ and $R_7$ preferably are alkyl having 1 to about 5 carbon atoms, aryl having 6 to about 14 carbon atoms, or aralkyl having 7 to about 15 carbon atoms. In preferred embodiments $R_6$ and $R_7$ are identical. However, it will be recognized that where $R_6$ and $R_7$ are not identical, the phosphorus atom presents an additional chiral center. M preferably is Li. It is believed that sodium and potassium salts should be avoided, as they have been found thusfar to not produce detectable amounts of product. The phosphite salts can be prepared by techniques known in the art, as, for example, in situ by reaction of n-butyllithium and diethyl phosphite.

Secondary aminophosphonates of formula V can be isolated and stored as free amines ($R_8$=H) or in protected form. Thus, in certain embodiments, $R_8$ is alkanoyl having 2 to 5 carbon atoms or alkoxycarbonyl having 2 to 5 carbon atoms. As will be recognized, alkanoyl groups are those wherein a carbonyl group bears an alkyl group and alkoxycarbonyl groups are those wherein a carbonyl group bears an -O-alkyl group.

Preferably, secondary aminophosphonates of formula V are directly reduced to provide the corresponding α-aminophosphonate. For example, secondary aminophosphonates can be hydrogenated in the presence of suitable catalysts. Surprisingly, it has been found that when $R_5$ is phenyl such hydrogenation proceeds with a high degree of regioselectivity to produce, for example, an R-isomer having formula I from the corresponding R,R-diastereomer having formula V. Preferred hydrogenation conditions include use of polar, protic solvent with a palladium catalyst such as Pd(OH)₂ at one atmosphere pressure of hydrogen gas.

Additional objects, advantages, and novel features of this invention will become apparent to those skilled in the art upon examination of the examples thereof provided below and in FIG. 1. Parts and percents are stated by weight unless otherwise indicated. Proton and carbon NMR were recorded on a Brucker AM500 spectrometer. Chemical shifts are reported in δ values relative to tetramethylsilane (δ=0) for proton spectra and relative to chloroform-d (δ=77.0) or acetone-d₆ (δ=29.8) for carbon spectra. Coupling constants are given in hertz. Specific rotations were collected on a Perkin Elmer polarimeter using chloroform or acetone solutions of aminophosphonates of known concentration. Diastereomeric excesses were determined either by capillary gas chromatography or by 500 MHz proton NMR. In each case, the relative ratio of diastereomers were derived by integration of peak areas. Authentic mixtures of diastereomers 8a and 9a, typically in a 2:1 ratio in favor of the R,R-diastereomer, were prepared by treating a benzene solution of imine 6a with diethylphosphite and catalytic anhydrous ZnCl₂ at room temperature. The mixtures thus produced were analyzed by proton NMR and capillary gas phase chromatography and were used to correlate retention times of the individual diastereomers during assays. Enantiomeric excesses were determined by conversion of the α-aminophosphonate to its (R)-Mosher amide (see, e.g., Dale, et al., *J. Org. Chem.* 1969, 34, 2543.) and the ratio of the diastereomers measured by proton NMR.

EXAMPLE 1

Preparation of Phosphoalanine (Formula Ia, R=Methyl).

To a solution of (R)-(-)-1-amino-1-phenyl-2-methoxyethane (202 mg, 1.333 mmol) in dry benzene (2 mL) at 0° C. was added freshly distilled acetaldehyde (0.3 mL). The mixture was allowed to warm to ambient temperature and treated with anhydrous sodium sulfate (1.5 g). After 1 h at room temperature, the mixture was filtered and concentrated to afford 212 mg (90%) of imine as a colorless oil that was used directly without further purification.

To a flame dried round bottomed flask was added distilled diethyl phosphite (308 μL, 2.393 mmol) and dry THF (1.5 mL) under an argon atmosphere. The mixture was cooled to 0° C. and treated dropwise with a hexane solution of n-butyllithium (1.59M; 0.72 mL, 1.137 mmol). After stirring for 0.5 h at 0° C., the mixture was warmed to room temperature and transferred onto a solution of the above imine (212 mg, 1.197 mmol) in tetrahydrofuran (THF, 2.4 mL). The mixture was stirred at room temperature for 21 h, quenched with water (5 mL) and the bulk of the THF removed in vacuo. The aqueous layer was saturated with sodium chloride and extracted with ethyl acetate (4×10 mL). The combined organic extracts were dried over sodium sulfate, filtered, and concentrated to leave 407 mg of yellow oil. Purification by flash chromatography (50 to 67% ethyl acetate-hexane) gave 275 mg (77%) of secondary aminophosphonate product as a colorless oil: $[\alpha]^{25}_D$ −1.5° (c 1.12, $CHCl_3$) ; IR ($CHCl_3$) 3010 (m) , 2920 (s) , 2870 (s) , 1505 (w), 1455 (s) , 1370 (s) , 1180 (s), 1125 (s) , 1075 (s), 910 (w) , 695 (m) , 595 (m), 570 (m) cm$^{-1}$; $^1$H NMR (500 MHz, $CDCl^3$) δ7.38 (dd, J=1, 7 Hz, 2 H), 7.32 (dt, J=1, 7 Hz, 2 H), 7.27 (m, 1 H), 4.40 (dt, J=2, 6 Hz, 1 H), 4.13 (m, 4 H), 3.38 (d, J=6 Hz, 2 H) , 3.37 (s, 3 H) , 2.83 (dq, $J_{HH}$=7 Hz, $J_{HP}$=10 Hz, 1 H) , 2.27 (br s, 1 H), 1.33 (q, J=7 Hz, 6 H), 1.23 (dd, $J_{HH}$=7 Hz, $J_{HP}$=17 Hz, 3.H) ; $^{13}$C NMR (125 MHz, $CDCl_3$) δ140.5, 128.3 (2), 127.7 (2), 127.5, 77.8, 61.9 (d, JCP=7 Hz) 61.6 (d, JCP=7 Hz), 60.3, 58.4, 47.9, 46.8, 17.4, 16.54, 16.52, 16.50, 16.4; high resolution mass spectrum (Cl, $CH_4$) m/z 316.1689 [(M+H)$^+$; calculate for $C_{15}H_{27}NO_4P$: 816.1677].

The above secondary aminophosphonate (86 mg, 0.273 mmol) was dissolved in absolute ethanol (6 mL) and treated with palladium hydroxide (86 mg). The flask was connected to a hydrogenation apparatus and the mixture thoroughly degassed and backfilled with hydrogen gas. The solution was stirred under hydrogen (1 atm) at room temperature for 23 h and then the catalyst was removed by filtration over Celite. Removal of solvent and purification of the residue by flash chromatography (5–10% methanol-chloroform) afforded 49 mg (99%) of α-aminophosphonate product as a colorless oil: $[\alpha]_D^{25}$ −5.4° (c 1.8, $CHCl_3$); IR ($CHCl_3$) 3009 (s), 2930 (m), 2860 (m), 1450 (w), 1360 (w) , 1200 (s) , 1062 (s), 920 (w) , 690 (m) cm$^{-1}$; $^1$H NMR (500 MHz, $CDCl_3$) δ4.15 (m, 4 H), 3.12 (m, 1 H), 1.68 (br s, 2 H), 1.35 (t, J=7.3 Hz, 6 H), 1.34 (q, $J_{HH}$=7.2 Hz, $J_{HP}$=17.6 Hz, 3 H); $_{13}$C NMR (125 MHz, $CDCl_3$) δ62.03 (d, JCP=6.86 Hz), 61.98 (d, $J_{CP}$=6.82 Hz), 44.12 (d, $J_{CP}$=149.6 Hz) , 17.19, 16.48 (d, $J_{CP}$=5.51 Hz, 2 C)

EXAMPLE 2

Preparation of α-Aminophosphonate Having Formula Ia, R=Cyclohexyl.

The procedure of Example 1 was repeated substituting one equivalent of cyclohexane carboxaldehyde for an excess of acetaldehyde. Results are shown in FIG. 1.

EXAMPLE 3

Preparation of α-Aminophosphonate Having Formula Ia, R=Cyclohexylmethyl.

The procedure of Example 1 was repeated substituting one equivalent of cyclohexylmethyl carboxaldehyde for an excess of acetaldehyde. Results are shown in FIG. 1.

EXAMPLE 4

Preparation of α-Aminophosphonate Having Formula Ia, R=Isopropyl.

The procedure of Example 1 was repeated substituting one equivalent of isobutyraldehyde for an excess of acetaldehyde. Results are shown in FIG. 1.

EXAMPLE 5

Preparation of α-Aminophosphonate Having Formula Ia, R=Isovaleryl.

The procedure of Example 1 was repeated substituting one equivalent of isovaleraldehyde for an excess of acetaldehyde. Results are shown in FIG. 1.

EXAMPLE 6

Preparation of α-Aminophosphonate Having Formula Ia, R=n-Hexyl.

The procedure of Example 1 was repeated substituting one equivalent of n-heptaldehyde for an excess of acetaldehyde. Results are shown in FIG. 1.

EXAMPLE 7

Preparation of α-Aminophosphonate Having Formula Ia, R=3-Thiomethylethyl.

The procedure of Example 1 was repeated substituting one equivalent of 3-thiomethylpropionaldehyde for an excess of acetaldehyde. Results are shown in FIG. 1.

EXAMPLE 8

Preparation of α-Aminophosphonate Having Formula Ia, R=Benzyloxymethyl.

The procedure of Example 1 was repeated substituting one equivalent of benzyloxyacetaldehyde for an excess of acetaldehyde. Results are shown in FIG. 1.

EXAMPLE 9

Preparation of α-Aminophosphonate Having Formula Ia, R=t-Butylpropionate.

The procedure of Example 1 was repeated substituting one equivalent of 4-oxobutanoic acid t-butyl ester for an excess of acetaldehyde. Results are shown in FIG. 1.

EXAMPLE 10

Preparation of α-Aminophosphonate Having Formula Ia, R=Phenyl.

The procedure of Example 1 was repeated substituting one equivalent of benzaldehyde for an excess of acetaldehyde. Lithium phosphite addition allowed to proceed for 48 h. Results are shown in FIG. 1.

EXAMPLE 11

Preparation of α-Aminophosphonate Having Formula Ia, R=2-Naphthyl.

The procedure of Example 1 was repeated substituting one equivalent of 2-naphthaldehyde for an excess of acetaldehyde. Lithium phosphite addition allowed to proceed for 48 h. Results are shown in FIG. 1.

EXAMPLE 12

Preparation of α-Aminophosphonate Having Formula Ia, R=Furyl.

The procedure of Example 1 was repeated substituting one equivalent of furfuraldehyde for an excess of acetaldehyde. Lithium phosphite addition allowed to proceed for 48 h. Results are shown in FIG. 1.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A synthetic process comprising the steps of:

contacting a primary amine compound having formula:

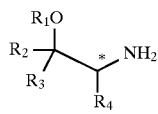

in the form of its R-isomer wherein:

$R_1$ is alkyl having 1 to about 10 carbon atoms or alkaryl having 7 to about 15 carbon atoms;

$R_2$ and $R_3$ are, independently, H, alkyl having 1 to about 10 carbon atoms, aryl having 6 to about 14 carbon atoms, or $R_2$ and $R_3$, together, are aryl or cycloalkyl;

$R_4$ is aryl having 6 to about 14 carbon atoms;

with an aldehyde having formula $R_5C(O)H$ for a time and under reaction conditions effective to form an imine compound having formula:

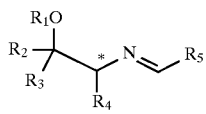

wherein:

$R_5$ is alkyl having 1 to about 10 carbon atoms; aryl having 6 to about 14 carbon atoms; aralkyl having 7 to about 15 carbon atoms; a naturally occurring amino acid sidechain; benzyloxymethyl; t-butylpropionate; furyl, or —(CH$_2$)$_n$—(CH=CH)$_x$—X wherein n is 1–5, x is 0 or 1, and X is hydrogen, alkyl having from 1 to about 10 carbon atoms, or aryl having 6 to about 14 carbon atoms;

contacting said imine compound with a phosphite compound having formula:

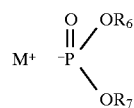

for a time and under reaction conditions effective to form a secondary aminophosphonate compound having formula:

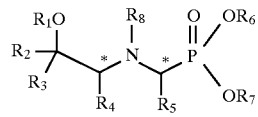

wherein:

M is Li;

$R_6$ and $R_7$ are, independently, H, alkyl having 1 to about 5 carbon atoms, aryl having 6 to about 14 carbon atoms, or aralkyl having 7 to about 15 carbon atoms;

$R_8$ is H, alkanoyl having 2 to about 5 carbon atoms or alkoxycarbonyl having 2 to about 5 carbon atoms; and said secondary aminophosphonate is in the form of its R,R-isomer with less than about 10% of its R,S-isomer; and contacting said secondary aminophosphonate compound for a time and under reducing conditions effective to form an α-aminophosphonate compound having formula:

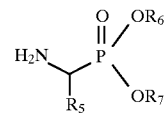

2. The process of claim wherein said reducing conditions include hydrogenation in the presence of a catalyst.

3. The process of claim 1 wherein less than about 5% of said R,S-isomer is present.

4. The process of claim 1 wherein less than about 2% of said R,S-isomer is present.

5. The process of claim 1 wherein $R_1$ is methyl.

6. The process of claim 1 wherein $R_4$ is phenyl.

7. The process of claim 1 wherein $R_5$ is cyclohexyl, cyclohexylmethyl, isopropyl, isovaleryl, n-hexyl, 2-thiomethylethyl, benzyloxymethyl, t-butylpropionate, phenyl, naphthyl, or furyl.

8. The process of claim 1 wherein $R_6$ and $R_7$ are both ethyl.

9. The process of claim 1 wherein $R_8$ is hydrogen.

10. The process of claim 1 wherein said phosphite is a lithium dialkyl phosphite.

* * * * *